(12) United States Patent
Shi

(10) Patent No.: US 12,141,747 B2
(45) Date of Patent: Nov. 12, 2024

(54) METHOD AND APPARATUS FOR ACQUIRING INVENTORY DATA, TERMINAL DEVICE AND COMPUTER-READABLE STORAGE MEDIUM

(71) Applicant: JINGDONG TECHNOLOGY INFORMATION TECHNOLOGY CO., LTD., Beijing (CN)

(72) Inventor: Yufeng Shi, Beijing (CN)

(73) Assignee: JINGDONG TECHNOLOGY INFORMATION TECHNOLOGY CO., LTD., Beijing (CN)

( * ) Notice: Subject to any disclaimer, the term of this patent is extended or adjusted under 35 U.S.C. 154(b) by 302 days.

(21) Appl. No.: 17/765,816

(22) PCT Filed: May 15, 2020

(86) PCT No.: PCT/CN2020/090660
§ 371 (c)(1),
(2) Date: Mar. 31, 2022

(87) PCT Pub. No.: WO2021/068507
PCT Pub. Date: Apr. 15, 2021

(65) Prior Publication Data
US 2022/0351122 A1    Nov. 3, 2022

(30) Foreign Application Priority Data
Oct. 12, 2019   (CN) .......................... 201910969928.3

(51) Int. Cl.
*G06Q 10/087* (2023.01)
*G06K 19/07* (2006.01)
(Continued)

(52) U.S. Cl.
CPC ....... *G06Q 10/087* (2013.01); *G06K 19/0723* (2013.01); *G16H 40/20* (2018.01);
(Continued)

(58) Field of Classification Search
CPC .. G06Q 10/087; G06Q 2220/00; G06Q 10/00; G06Q 10/08; G06Q 10/0875;
(Continued)

(56) References Cited

U.S. PATENT DOCUMENTS

2016/0342938 A1   11/2016   Tian et al.
2019/0156440 A1   5/2019    Wang et al.

FOREIGN PATENT DOCUMENTS

| CN | 101957938 A | 1/2011 |
| CN | 104794507 A | 7/2015 |

(Continued)

OTHER PUBLICATIONS

First Office Action issued in counterpart Chinese Patent Application No. 201910969928.3, dated Apr. 6, 2022.
(Continued)

*Primary Examiner* — Garcia Ade
(74) *Attorney, Agent, or Firm* — Westbridge IP LLC

(57) ABSTRACT

Disclosed are a method and an apparatus for acquiring inventory data, a terminal device and a computer-readable storage medium. The method comprises: receiving a request for inventory data sent by a terminal device, where electronic tag data of the target item being carried in the request for inventory data; according to the inventory data request, searching among inventory record data pre-stored in a blockchain network for target inventory data corresponding to the electronic tag data, where the target inventory data being corresponding to the target item; and sending the target inventory data to the terminal device.

14 Claims, 6 Drawing Sheets

(51) Int. Cl.
*G16H 40/20* (2018.01)
*H04L 9/00* (2022.01)

(52) U.S. Cl.
CPC ........... *H04L 9/50* (2022.05); *G06Q 2220/00* (2013.01); *H04L 2209/805* (2013.01)

(58) Field of Classification Search
CPC ........... G06K 19/0723; G06K 17/0029; G16H 40/20; H04L 9/50; H04L 2209/805
USPC .......................................................... 705/28
See application file for complete search history.

(56) References Cited

FOREIGN PATENT DOCUMENTS

| | | | | |
|---|---|---|---|---|
| CN | 105243530 A | | 1/2016 | |
| CN | 105956808 A | | 9/2016 | |
| CN | 107657418 A | | 2/2018 | |
| CN | 108090725 A | | 5/2018 | |
| CN | 108470265 A | * | 8/2018 | ............. G06F 16/25 |
| CN | 108960366 A | | 12/2018 | |
| CN | 110321336 A | | 10/2019 | |
| CN | 110889657 A | | 3/2020 | |
| CN | 111008681 A | * | 4/2020 | ....... G06K 19/07749 |
| JP | 2010044723 A | | 2/2010 | |
| WO | 2016151594 A1 | | 9/2016 | |
| WO | 2019184210 A1 | | 10/2019 | |

OTHER PUBLICATIONS

European Search Report issued in counterpart European Patent Application No. EP 20875019.0, dated Aug. 29, 2022.
International Search Report and Written Opinion issued in corresponding PCT Application No. PCT/CN2020/090660, dated Jul. 29, 2020.
Notice of Reasons for Refusal issued in counterpart Japanese Patent Application No. JP 2022-519838, dated Jul. 25, 2023.
Notification to Grant Patent Right for Invention issued in counterpart Japanese Patent Application No. JP 2022-519838, dated Jan. 23, 2024.
Refusal Decision issued in counterpart Chinese Patent Application No. 201910969928.3, dated Jan. 9, 2023.
Second Office Action issued in counterpart Chinese Patent Application No. 201910969928.3, dated Sep. 5, 2022.
Song et al., Chain Enterprise Information Management, 2016, p. 136, Fudan University Press, Shanghai, dated Jul. 30, 2016.
Zhou, Introduction to E-Commerce, 2019, p. 20, Southeast University Press, Nanjing, dated Jan. 31, 2019.

* cited by examiner

METHOD AND APPARATUS FOR ACQUIRING INVENTORY DATA, TERMINAL DEVICE AND COMPUTER-READABLE STORAGE MEDIUM

CROSS-REFERENCE TO RELATED APPLICATIONS

This application is the National Stage of International Application No. PCT/CN2020/090660, filed on May 15, 2020, which claims priority to Chinese Patent Application No. 201910969928.3, entitled "METHOD AND APPARATUS FOR ACQUIRING INVENTORY DATA, TERMINAL DEVICE AND STORAGE MEDIUM", filed on Oct. 12, 2019, the entire contents of which are incorporated herein by reference.

TECHNICAL FIELD

This present disclosure relates to the field of blockchain technology, and in particular, relates to a method and an apparatus for acquiring inventory data, a terminal device and a computer-readable storage medium.

BACKGROUND

Since various circulation links are involved when medicines are entering or leaving a pharmacy, the inventory data of the medicines in each of the circulation links is usually to be recorded, in order to facilitate effective management of the medicines.

It is usually necessary to use the results of periodic inventory of medicines, and on this basis, to count the inventory data according to the storage and delivery of the medicines. However, in the process of implementing the present disclosure, the inventors found that the inventory data of related technology statistics has the defect of inaccurate data. When faults occur to medicines in any circulation link, the workload of staff to count the inventory data will be increased, which results in prolonged statistical cycle of inventory data, reduced statistical efficiency, higher labor costs and time costs, and inaccurate statistical inventory data.

In view of the above-mentioned problems, no effective solutions have yet been proposed.

SUMMARY

In order to solve or at least partially solve the above-mentioned technical problems, the embodiments of the present disclosure provide a method and an apparatus for acquiring inventory data, a terminal device, and a computer-readable storage medium.

In view of the above, in the first aspect, an embodiment of the present disclosure provides a method for acquiring inventory data, the method includes steps of:
receiving a request for inventory data sent by a terminal device, where electronic tag data of a target item is carried in the request for inventory data;
searching, according to the request for inventory data, among inventory record data pre-stored in a blockchain network for target inventory data corresponding to the electronic tag data, where the target inventory data corresponds to the target item;
sending the target inventory data to the terminal device.

With reference to the first aspect, in the first possible implementation mode of the first aspect, the target inventory data includes placement inventory data and shelf inventory data of the target item, and before sending the target inventory data to the terminal device, the method further includes the following step:
counting a first accumulated value of the placement inventory data and shelf inventory data;
where sending the target inventory data to the terminal device includes the following step:
sending the first accumulated value of the placement inventory data and the shelf inventory data to the terminal device.

With reference to the first aspect, in the second possible implementation mode of the first aspect, the target inventory data includes historical placement inventory data, pending placement inventory data, and placement completion data of the target item. The placement inventory data is determined in ways of:
counting a second accumulated value of the historical placement inventory data and the pending placement inventory data;
counting a first difference value between the second accumulated value and the placement completion data;
determining the placement inventory data according to the first difference value.

With reference to the first aspect, in the third possible implementation mode of the first aspect, the target inventory data includes historical shelf inventory data, warehousing data, out of warehousing data, and loss report data of the target item, and the shelf inventory data is determined in ways of:
counting a third accumulated value of the historical shelf inventory data and the warehousing data;
counting a second difference value between the third accumulated value and a sum of the out of warehousing data and the loss report data;
determining the shelf inventory data according to the second difference value.

With reference to the first aspect, in the fourth possible implementation mode of the first aspect, before sending the target inventory data to the terminal device, the method further includes the following steps:
acquiring releasing time of the target item;
counting the time interval between the releasing time and a preset expiration date of a validity period for the target item;
where sending the target inventory data to the terminal device includes the following step:
sending a picking request when the time interval is less than a preset time interval threshold, where the picking request is used to request a picking operation for the target item.

With reference to the first aspect, in the fifth possible implementation mode of the first aspect, the method further includes the following steps:
receiving inventory change data of the target item;
updating the inventory record data in the blockchain network according to the inventory change data.

In the second aspect, an embodiment of the present disclosure provides a method for acquiring inventory data, which is applied to a terminal device, and the method includes the following steps:
sending a request for inventory data to a server, where electronic tag data of a target item is carried in the request for inventory data;

receiving target inventory data sent by the server, where the target inventory data is searched by the server among inventory record data pre-stored in a blockchain network according to the request for inventory data, where the target inventory data corresponds to the target item.

With reference to the second aspect, in the first possible implementation mode of the second aspect, the sending of a request for inventory data to the server includes the following step:

sending the request for inventory data to the server by calling a chain code and executing a smart contract.

In the third aspect, an embodiment of the present disclosure provides an apparatus for acquiring inventory data, which is applied to a server, and the apparatus includes the following units:

a first receiving unit configured to receive a request for inventory data sent by a terminal device, where electronic tag data of a target item is carried in the request for inventory data;

a searching unit configured to search, according to the request for inventory data, among the inventory record data pre-stored in a blockchain network for target inventory data corresponding to the electronic tag data, where the target inventory data corresponds to the target item; and a first sending unit configured to send the target inventory data to the terminal device.

In the fourth aspect, an embodiment of the present disclosure provides an apparatus for acquiring inventory data, which is applied to a terminal device, and the apparatus includes the following units:

a second sending unit configured to send a request for inventory data to a server, where electronic tag data of a target item is carried in the request for inventory data;

a second receiving unit configured to receive target inventory data sent by the server, where the target inventory data is searched by the server among inventory record data pre-stored in a blockchain network according to the request for inventory data, where the target inventory data corresponds to the target item.

In the fifth aspect, an embodiment of the present disclosure provides a terminal device, the terminal device includes at least one processor, one memory, at least one network interface and one user interface;

the at least one processor, one memory, at least one network interface and one user interface are coupled together through a bus system.

the processor is used to execute the steps of the method for acquiring inventory data as described in the first or the second aspect by calling the program or instruction stored in the memory.

In the sixth aspect, an embodiment of the present disclosure provides a computer-readable storage medium, the computer-readable storage medium stores a program for acquiring inventory data, and when the program for acquiring inventory data is executed by a processor, the methods for acquiring inventory data as described in the first aspect or the second aspect are implemented.

The above-mentioned embodiments of the present disclosure have the following advantages.

The embodiments of the present disclosure provide a method, an apparatus, a terminal device and a storage medium for acquiring inventory data. The method for acquiring inventory data receives a request for inventory data of a target item sent by a terminal device, where the request for inventory data carries electronic tag data of the target item; searching, according to the request for inventory data, among inventory record data pre-stored in a blockchain network for target inventory data corresponding to the electronic tag data, where the target inventory data corresponds to the target item; sending the target inventory data to a terminal device.

In the embodiments of the present disclosure, identify a target item is identified by using electronic tag data. Due to the advantages of fast scanning, reusability, large data storage capacity, durability and security, etc., the electronic tag can identify data by fast scanning and through one item one code, which improves data processing efficiency. Real-time sharing, openness and transparency, and traceability of various circulation links of inventory data is realized by using the traceable, decentralized, de-creditable, and non-tamperable distributed accounting mechanism of blockchain network, thereby increasing the statistical efficiency and accuracy of the inventory data and reducing labor costs and time costs.

BRIEF DESCRIPTION OF THE DRAWINGS

The drawings herein are incorporated into and constitute a part of the specification, show embodiments that conform to the present disclosure, and are used together with the specification to explain the principle of the present disclosure.

In order to more clearly describe the embodiments of the present disclosure, the accompanying drawings that need to be used in the description of the embodiments will be briefly introduced in the following. It is apparent to those persons of ordinary skill in the art that other drawings can be obtained based on these drawings without paying creative work.

DETAILED DESCRIPTION OF THE EMBODIMENTS

In order to make the purpose, technical solutions and advantages of the embodiments of the present disclosure clearer, the technical solutions in the embodiments of the present disclosure will be described clearly and completely below in combination with the accompanying drawings in the embodiments of the present disclosure. Obviously, the described embodiments are a part not all of the embodiments of the present disclosure. Based on the embodiments of the present disclosure, all other embodiments obtained by those persons of ordinary skill in the art without paying creative work shall fall within the protection scope of this disclosure.

A server implementing various embodiments of the present disclosure will now be described with reference to the accompanying drawings. In the following description, the use of suffixes such as "module", "part" or "unit" used to indicate elements is only for the benefit of the description of the application, which has no specific meaning in itself. Therefore, "modules" and "parts" can be mixed.

Figure 1:
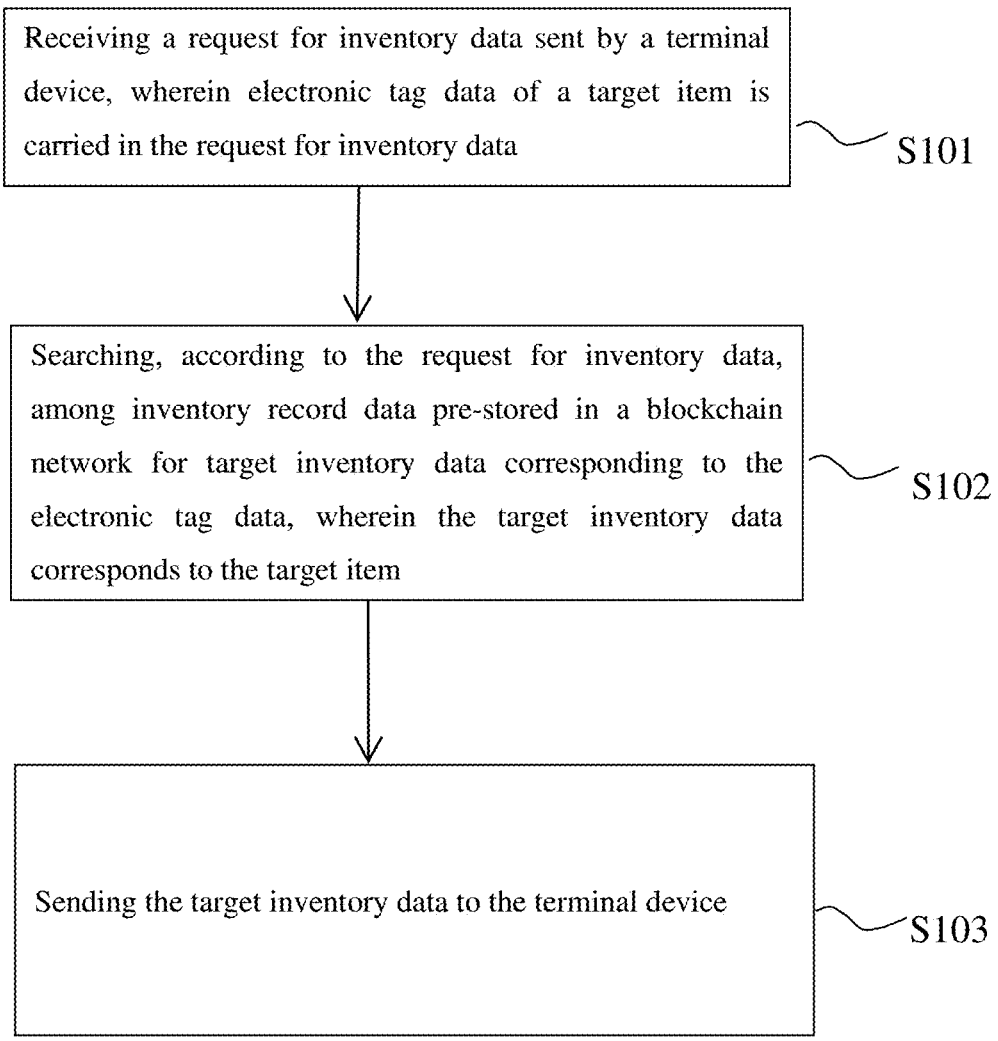
FIG. 1 is a schematic flowchart of a method for acquiring inventory data according to an embodiment of the present disclosure.

An embodiment of the present disclosure provides a method for acquiring inventory data, which is applied to a server. As shown in FIG. 1, the method may include the following steps S101 to S103.

Step S101: receiving a request for inventory data sent by a terminal device, where the request for inventory data carries electronic tag data of the target item.

Figure 2:
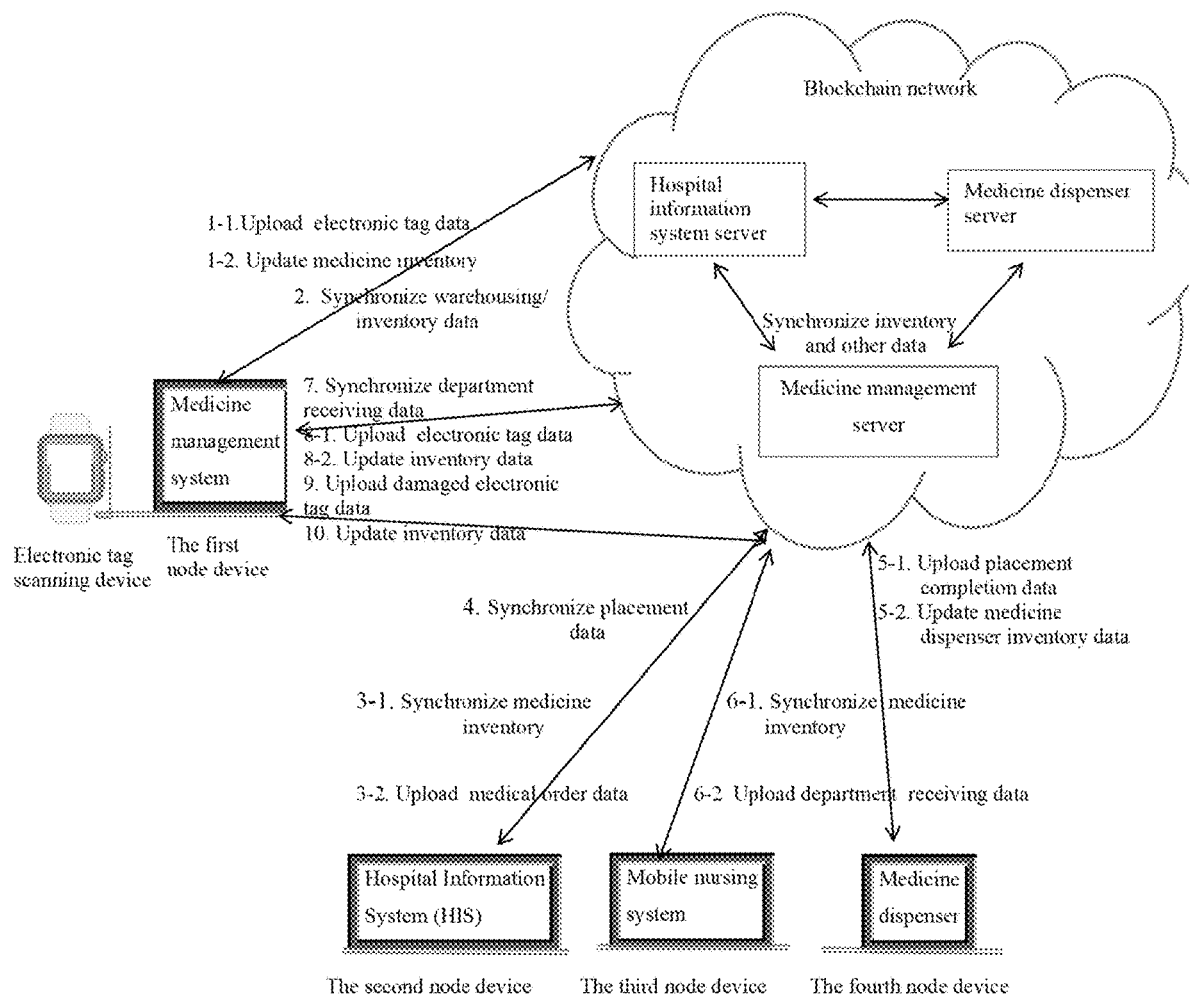
FIG. 2 is an implementation schematic diagram according to an embodiment of the present disclosure.

As shown in FIG. 2, which is an implementation schematic diagram of this embodiment of this disclosure: the connected hospital information system server, item subcontracting server, and item management server are deployed in a blockchain network. To be noted, items include but are not limited to medicine; the item subcontracting server may be a medicine dispenser server, and the item management server may be a medicine management server. Multiple node devices are connected to the blockchain network, the types of node devices include but are not limited to the first node device deployed with an item management system, the second node device deployed with an HIS (Hospital Information System), the third node device deployed with an item mobile nursing system, and the fourth node device deployed with an item placement program, the item management system may be a medicine management system, and the fourth node device may be a medicine dispenser deployed with a medicine dispensing program, where the request for inventory data may be sent by each node device, and each node device acquires and synchronizes inventory data through the blockchain network.

In the embodiments of the present disclosure, when medicines are warehoused, the electronic tag data is acquired by scanning the electronic tags on the medicine by the electronic tag scanning device, and the electronic tag data of all the scanned warehousing medicine are stored in the blockchain network. The electronic tag data includes but is not limited to: medicine warehousing department, electronic tag ID, medicine name, medicine type, expiration date of medicine batch number, medicine quantity and other information. Electronic tags have the advantages of one item and one code, which is convenient to scan, identify and trace the inventory data of medicines.

The electronic tags in the embodiments of the present disclosure include but are not limited to RFID (Radio Frequency Identification) electronic tags.

After confirming the medicine warehousing information, call the system chain code, execute the smart contract, update the medicine inventory data, merge it into the linked storage, synchronize between each node device, and the entire process inventory data of the medicine circulating between each system is public and transparent, and cannot be tampered, thereby ensuring the security and effectiveness of data and ensuring that the inventory data stored in the blockchain network is consistent with the actual medicine inventory data. The accurate inventory data is convenient for reference and analysis of inventory data, plans to increase or decrease inventory based on the analysis results of inventory data can also be formulated so as to automatically count inventory data, which only needs manual verification, improves efficiency and saves labor costs and time costs.

Users can view the electronic tag data of the medicine that have been warehoused and the medicine inventory information in real time through each node device, including but not limited to the placement inventory data and shelf inventory data, where the placement inventory data is the inventory data of medicine dispenser, the replenishment plan can be formulated according to the medicine inventory information, so as to realize the inventory management of the medicine.

The terminal device of the embodiments of the present disclosure can be implemented in various forms. To be noted, the terminal devices described herein may include mobile terminals such as mobile phones, tablet computers, notebook computers, palmtop computers, PDA (Personal Digital Assistant), PMP (Portable Media Player), navigation devices, wearable devices, smart bracelets and pedometers, as well as fixed terminals such as digital TVs and desktop computers.

The following description will take mobile terminals as an example. Those skilled in the art will understand that, in addition to elements specifically intended for mobile purposes, the construction according to the embodiments of the present disclosure can also be applied to fixed-type terminal devices.

Step S102: Searching, according to the request for inventory data, among inventory record data pre-stored in the blockchain network for the target inventory data corresponding to the electronic tag data, where the target inventory data corresponds to the target item.

Step S103: sending the target inventory data to the terminal device.

The embodiments of the present disclosure identify the target item by using electronic tag data. Due to the advantages of fast scanning, reusability, large data storage capacity, durability and security, etc., the electronic tag can identify data by fast scanning and through one item one code, which improves data processing efficiency. Real-time sharing, openness and transparency, and traceability of various circulation links of inventory data is realized by using the traceable, decentralized, de-creditable, and non-tamperable distributed accounting mechanism of blockchain network, thereby increasing the statistical efficiency and accuracy of the inventory data and reducing labor costs and time costs.

In order to facilitate the understanding of the embodiments of the present disclosure, specific embodiments are described as follows.

Figure 3:
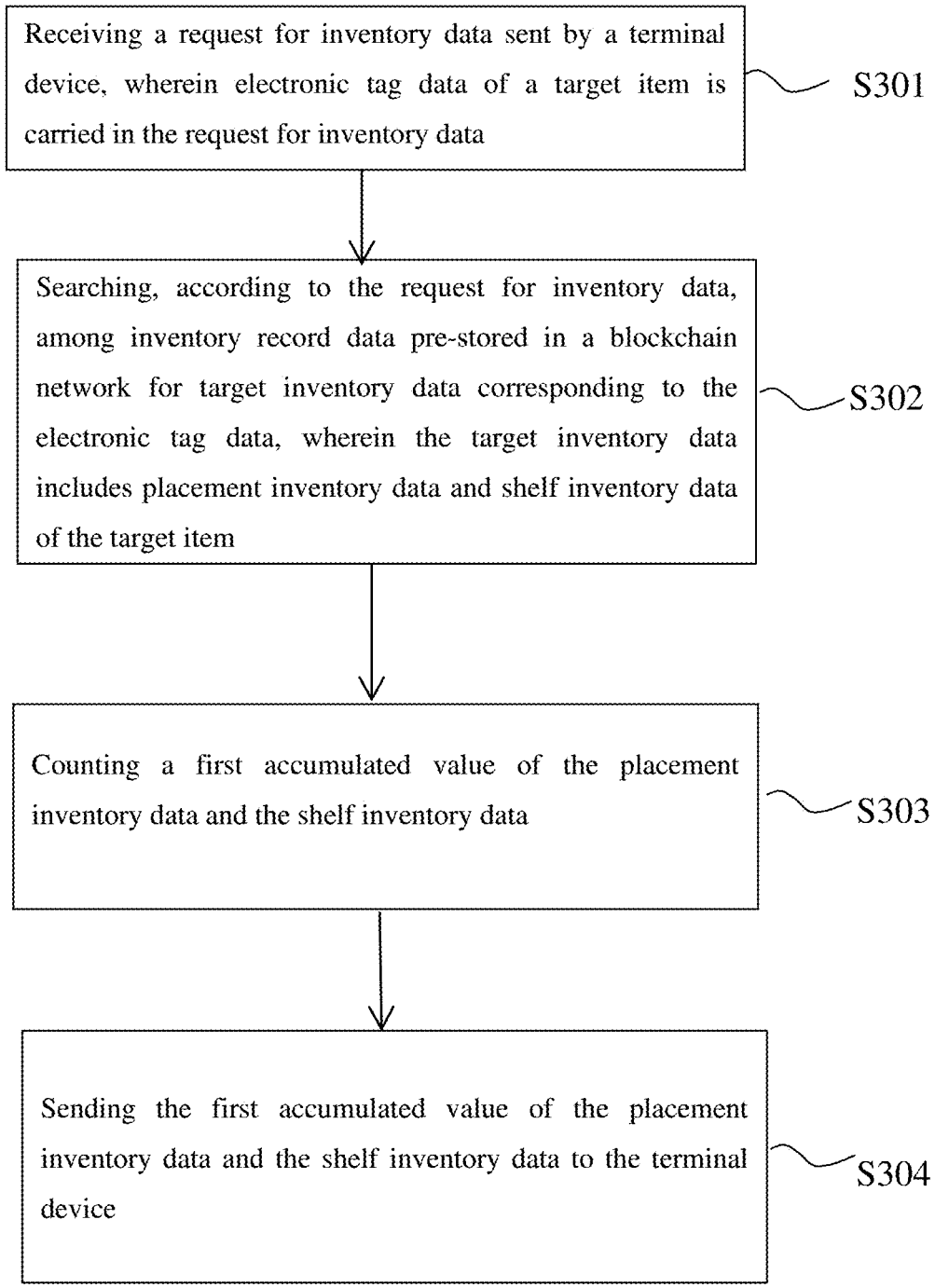
FIG. 3 is a schematic flowchart of another method for acquiring inventory data according to an embodiment of the present disclosure.

As shown in FIG. 3, it shows another method for acquiring inventory data applied to a server, and the method includes the following steps S301 to S304.

Step S301: receiving a request for inventory data sent by a terminal device, where the request for inventory data carries electronic tag data of the target item.

Step S302: searching, according to the request for inventory data, among inventory record data pre-stored in the blockchain network for target inventory data corresponding to the electronic tag data, where the target inventory data includes the placement inventory data and shelf inventory data of the target item.

In this embodiment, the target inventory data corresponds to the target item, each medicine has a unique electronic tag data, and each electronic tag data corresponds to an inventory data of the medicine, which is convenient for scanning, identifying and viewing the inventory data.

Step S303: counting the first accumulated value of the placement inventory data and the shelf inventory data.

The inventory data of medicine is the sum of the placement inventory data of the medicine dispenser and the shelf inventory data. The placement inventory data can be construed as the number of medicine waiting for the medicine dispenser to perform medicine dispensing operation, and the shelf inventory data can be construed as the medicine in warehouse. To be noted, if the placement inventory data is 100 and the shelf inventory data is 300, then the first accumulated value 400 is obtained by accumulating the placement inventory data and the shelf inventory data, that is, the inventory data of the target medicine is 400.

It should be noted that although the placement inventory data and shelf inventory data are illustrated above with examples, those skilled in the art should understand that it is also possible to continue to set other values for placement inventory data and shelf inventory data to meet the statistical requirements of inventory data, the embodiments of the present disclosure are not limited to this.

Step S304: sending the first accumulated value of the placement inventory data and the shelf inventory data to the terminal device.

In some embodiments of the present disclosure, the target inventory data includes historical placement inventory data, pending placement inventory data, and placement completion data of the target item, and the placement inventory data is determined in ways of:
  counting the second accumulated value of the historical placement inventory data and the pending placement inventory data;
  counting the first difference value between the second accumulated value and the placement completion data;
  determining the placement inventory data according to the first difference value.

In some embodiments of the present disclosure, the historical placement inventory data is the original inventory data of the medicine dispenser, or it can be understood as the quantity of historical medicine to be placed, and the inventory data of pending placement can be understood as the quantity of newly replenished medicine to be placed, the placement completion data can be understood as the quantity of the medicines that have been placed, for example, historical placement inventory data is 80, pending placement inventory data is 50, placement completion data is 30, and the second accumulated value 130 is obtained by accumulating historical placement inventory data and pending placement inventory data. The first difference value 100 is obtained by calculating the difference between the second accumulated value and the placement completion number, that is, the placement inventory data of the medicine dispenser is 100, and there are 100 medicines waiting for the medicine dispenser to perform dispensing operation.

The medicine dispenser performs medicine dispensing operation through the medical order data synchronized by the blockchain network. It can monitor the medicine dispensing status of the medicine dispenser in real time. The medicine dispensing completion data is uploaded to the blockchain network upon completion of despensing the medicine. The chain code is called to update the inventory data of the medicine dispenser, and synchronization is performed between the node devices. There is separate inventory for the medicine at the medicine dispenser; when the medicine is being replenished, the electronic tags of the medicine can be scanned for releasing, where the shelf inventory data is decreased, and the placement inventory data of the medicine dispenser is increased.

It should be noted that although the historical placement inventory data, pending placement inventory data and placement completion data are illustrated above with examples, those skilled in the art should understand that it is also possible to continue to set other values for the historical placement inventory data, pending placement inventory data and placement completion data to meet the statistical requirements of inventory data, the embodiments of the present disclosure are not limited to this.

In some embodiments of the present disclosure, the target inventory data includes historical shelf inventory data, warehousing data, out of warehousing data, and loss report data of the target item, and the shelf inventory data is determined in ways of:
  counting the third accumulated value of the historical shelf inventory data and the warehousing data;
  counting the second difference value between the third accumulated value and the sum of the out of warehousing data and the loss report data;
  determining the shelf inventory data according to the second difference value.

The doctor can view the inventory data of the medicine in real time when issuing a medical order data so as to assist doctors to make corresponding medical order plans according to the inventory data of medicine. After the medical order data is confirmed and executed, the medical order data will be uploaded to the blockchain network for storage and the data is synchronized between the node devices connected to the blockchain network. When receiving medicine, nurses can view the inventory data of medicine in real time through the third node device deployed with an item mobile nursing system; the nurse can make a plan for receiving medicine in the department according to the real-time inventory of the medicine. After the medicine is confirmed to be received, the receiving data is uploaded to the blockchain network to update the inventory data; the medicine picker can view the medicine receiving data of the department in real time on the first node device where the item management system is deployed, and make a medicine releasing plan, as a guide for manual medicine picking. After medicine picking, the electronic tag of the medicine is scanned through the electronic tag scanning device and after confirming medicine release, the electronic tag data of medicine is uploaded to the blockchain network so as to update the inventory data of the medicine picked.

It should be noted that if the electronic tag of the medicine is damaged, the damaged electronic tag can be scanned by the electronic tag scanning device and the loss report data of the medicine can be uploaded; if the electronic tag cannot be identified, the damaged tag can be traced by scanning the tag of such medicine in warehouse.

It should be noted that if the medicine is borrowed offline, it can be identified by the electronic tag scanning device when released and a reminder signal will be issued to remind that the medicine is released offline, which is convenient for verification.

In some embodiments of the present disclosure, before sending the target inventory data to the terminal device, the method further includes the following steps:
  acquiring the time of releasing of the target item;
  counting the time interval between the releasing time and the preset expiration date of the validity period for the target item;
  where the sending of the target inventory data to the terminal device includes:
  when the time interval is less than the preset time interval threshold, a picking request is sent, and the picking request is used to request a picking operation for the target item.

In some embodiments of the present disclosure, an automatic statistics of the inventory data of medicine can be realized by scanning the electronic tags of medicine in warehouse. The statistical time can be shortened to a few minutes, thus improving the statistical efficiency. When releasing medicines and scanning the electronic tag of the medicines to be released, it will automatically detect whether there is a medicine close to the expiration date among the medicines to be released, that is, calculating the time interval between the releasing time and the preset expiration date of the validity period for the target item. When the time interval is less than the preset time interval threshold, it indicates that there is a medicine close to the expiration date in the medicines to be released, and then a picking request is sent to remind the pickers to give priority to picking the medicine close to the expiration date so as to speed up the releasing efficiency.

In some embodiments of the present disclosure, the method further includes the following steps:

receiving inventory change data of the target item;

using the inventory change data to update the inventory record data in the blockchain network.

Figure 4:
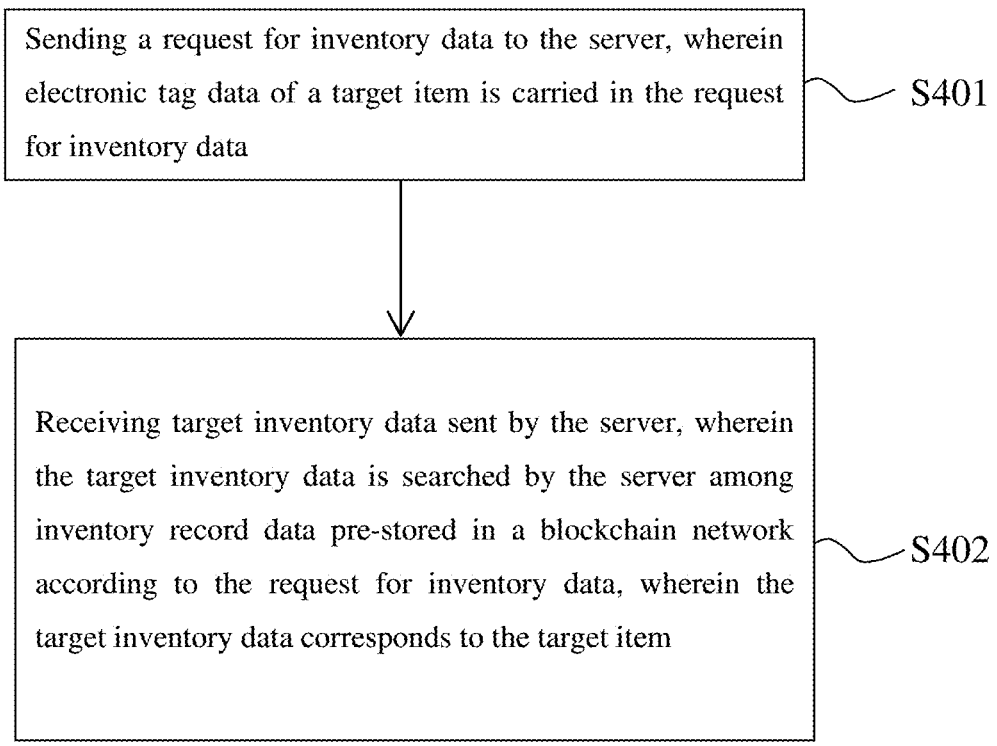
FIG. 4 is a schematic flowchart of another method for acquiring inventory data according to an embodiment of the present disclosure.

As shown in FIG. 4, it shows another method for acquiring inventory data applied to a terminal device. The method includes the following steps S401 and S402.

Step S401: sending a request for inventory data to a server, where the request for inventory data carries electronic tag data of the target item.

Step S402: receiving target inventory data sent by the server, where the target inventory data is searched by the server among the inventory record data pre-stored in the blockchain network according to the request for inventory data, where the target inventory data corresponds to the target item.

In some embodiments of the present disclosure, the sending of a request for inventory data to a server in the foregoing step S401 includes the following step:

sending the request for inventory data to the server by calling the chain code and executing the smart contract.

Figure 5:
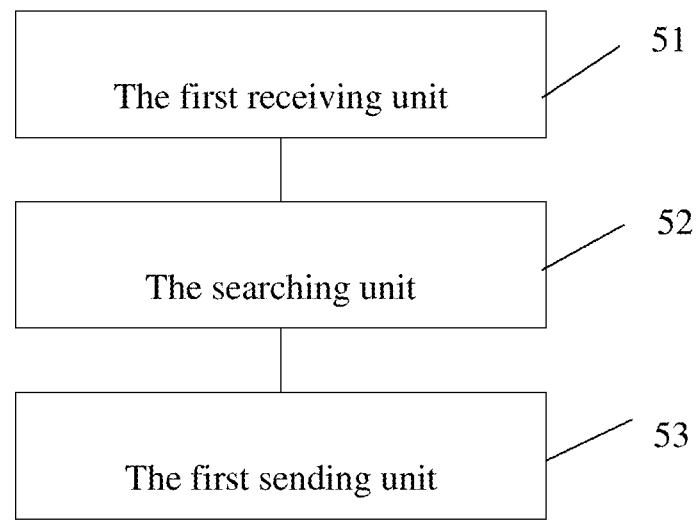
FIG. 5 is a schematic structural diagram of an apparatus for acquiring inventory data according to an embodiment of the present disclosure.

As shown in FIG. 5, it shows an apparatus for acquiring inventory data applied to a server, and the apparatus includes the following units 51 to 53:

the first receiving unit 51 is configured to receive a request for inventory data sent by a terminal device, where the request for inventory data carries electronic tag data of the target item;

the searching unit 52 is configured to search among the inventory record data pre-stored in the blockchain network for the target inventory data corresponding to the electronic tag data, where the target inventory data corresponds to the target item;

the first sending unit 53 is configured to send the target inventory data to the terminal device.

Figure 6:
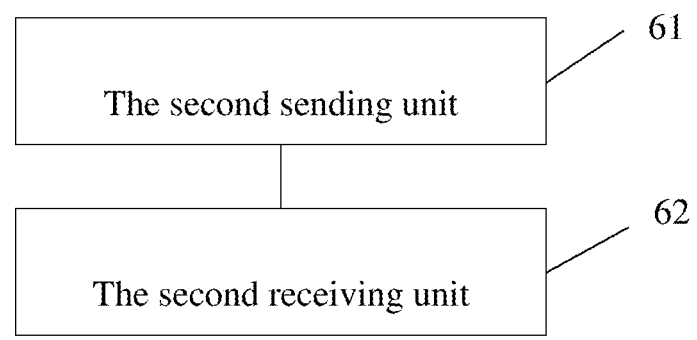
FIG. 6 is a schematic structural diagram of an apparatus for acquiring inventory data according to an embodiment of the present disclosure.

As shown in FIG. 6, it shows an apparatus for acquiring inventory data applied to a terminal device, and the apparatus includes the following units 61 and 62:

the second sending unit 61 is configured to send a request for inventory data to a server, where the request for inventory data carries electronic tag data of the target item;

the second receiving unit 62 is configured to receive target inventory data sent by the server, where the target inventory data is searched by the server among inventory record data pre-stored in the blockchain network according to the request for inventory data, where the target inventory data corresponds to the target item.

Figure 7:
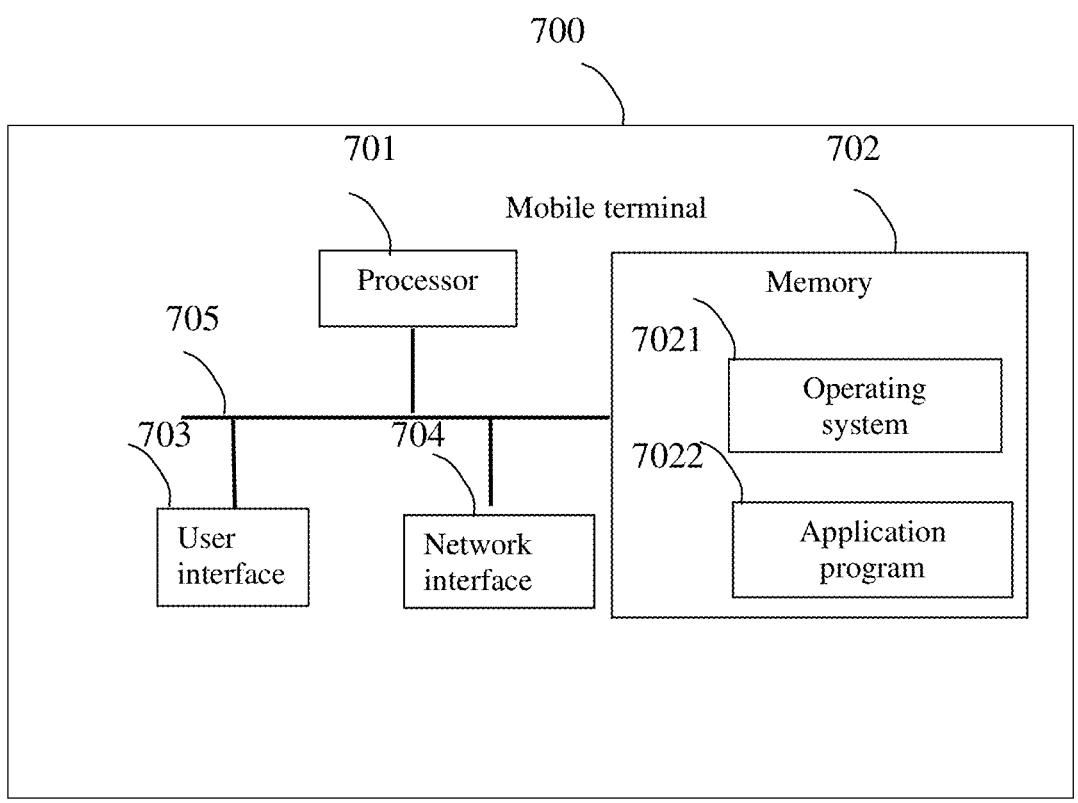
FIG. 7 is a schematic structural diagram of a mobile terminal according to an embodiment of the present disclosure.

FIG. 7 is a schematic structural diagram of a mobile terminal provided by another embodiment of the present disclosure. The mobile terminal 700 shown in FIG. 7 includes: at least one processor 701, one memory 702, at least one network interface 704, and another user interface 703. The various components in the mobile terminal 700 are coupled together through the bus system 705. It can be understood that the bus system 705 is used to implement connection and communication between these components. In addition to the data bus, the bus system 705 also includes a power bus, a control bus, and a status signal bus. However, for the sake of clear description, various buses are marked as the bus system 705 in FIG. 4.

The user interface 703 may include a display, a keyboard, or a pointing device (for example, a mouse, a trackball, a touch panel, or a touch screen, etc.).

It can be understood that the memory 702 in the embodiments of the present disclosure may be a volatile memory or a non-volatile memory, or may include both of them, where the non-volatile memory can be read-only memory (ROM), programmable ROM (PROM), erasable PROM (EPROM), electrically EPROM (EEPROM) or flash memory. The volatile memory may be random access memory (RAM), which is used as an external cache. By way of exemplary but not restrictive description, many forms of RAM are available, such as static RAM (SRAM), dynamic RAM (DRAM), synchronous DRAM (SDRAM), double data rate SDRAM (DDRSDRAM), enhanced SDRAM (ESDRAM), synchlink DRAM (SLDRAM) and direct rambus RAM (DRRAM). The memory 702 described herein is intended to include, but is not limited to, these and any other suitable types of memory.

In some embodiments of the present disclosure, the memory 702 stores the following elements, executable units or data structures, or their subsets, or their extended sets: operating system 7021 and application programs 7022.

The operating system 7021 includes various system programs, such as a framework layer, a core library layer and a driver layer, etc., for implementing various basic services and processing hardware-based tasks. The application program 7022 includes various application programs, such as a media player, a browser, etc., which are used to implement various application services. The program for implementing a method of one of the embodiments of the present disclosure may be included in the application program 7022.

In some embodiments of the present disclosure, the processor 701 is used to execute the method steps provided in each embodiment by calling a program or instructions stored in the memory 702. In some embodiments of the present disclosure, a program or instructions stored in the application program 7022 may include:

receiving a request for inventory data sent by a terminal device, where the request for inventory data carries electronic tag data of the target item;

searching, according to the request for inventory data, among the inventory record data pre-stored in the blockchain network for the target inventory data corresponding to the electronic tag data, where the target inventory data corresponds to the target item;

sending the target inventory data to the terminal device.

The method disclosed in the foregoing embodiments of the present disclosure may be applied to the processor 701 or implemented by the processor 701. The processor 701 may be an integrated circuit chip with signal processing capabilities. In the process of implementation, the steps of the foregoing method can be completed by an integrated logic circuit of hardware in the processor 701 or instructions in the form of software. The aforementioned processor 701 may be a general-purpose processor, a digital signal processor (DSP), an application specific integrated circuit (ASIC), a field programmable gate array (FPGA) or other programmable logic devices, discrete gates or transistor logic devices and discrete hardware components, which can implement or execute the methods, steps, and logical block diagrams disclosed in the embodiments of the present disclosure. The general-purpose processor may be a microprocessor or the processor may also be any conventional processor or the like. The steps of the method disclosed in combination with the embodiments of the present disclosure may be directly embodied as completed execution by a hardware decoding processor, or executed and completed by a combination of hardware and software units in the decoding processor. The software unit may be located in a mature storage medium in the field, such as random access memory, flash memory, read-only memory, programmable read-only memory, or electrically erasable programmable memory and registers. The storage medium is located in the memory 702, the processor 701 reads the information in the memory 702, and completes the steps of the foregoing method in combination with its hardware.

It can be understood that the embodiments described herein can be implemented by hardware, software, firmware, middleware, microcode, or a combination thereof. For hardware implementation, the processing unit can be implemented in one or more application specific integrated circuits (ASIC), digital signal processing (DSP), digital signal processing device (DSPD), programmable logic device (PLD), field-programmable gate array (FPGA), general-purpose processors, controllers, microcontrollers, micropro-cessors, other electronic units for performing the functions described in the present disclosure, or combinations thereof.

For the implementation of software, the technology described herein can be implemented by a unit that performs the functions described herein. The software codes can be stored in the memory and executed by the processor. The memory can be implemented in or outside the processor.

An embodiment of the present disclosure also provides a computer-readable storage medium and the computer-readable storage medium stores a program for acquiring inventory data. When the program for acquiring inventory data is executed by the processor, it's implemented as described in each method embodiment. The steps mentioned may include:

receiving a request for inventory data sent by a terminal device, where the request for inventory data carries electronic tag data of the target item;

searching, according to the request for inventory data, among the inventory record data pre-stored in the blockchain network for the target inventory data corresponding to the electronic tag data, where the target inventory data corresponds to the target item;

sending the target inventory data to the terminal device.

For the convenience of description, when describing the above device, the functions are divided into various units and described separately. Of course, when implementing the present disclosure, the functions of each unit can be implemented in the same or more software and/or hardware.

The embodiments of the present disclosure are described in a progressive manner, and the same or similar parts between various embodiments can be referred to each other, and the emphasis of each embodiment is the difference from other embodiments. In particular, for the apparatus or system embodiment, it's simply described since it is basically similar to the method embodiment, and the relevant part can refer to the partial description of the method embodiment. The above-described apparatus and system embodiments are merely illustrative, where the units described as separate components may or may not be physically separated, and the components displayed as units may or may not be physical units, that is, it can be located in one place or distributed over multiple network units. Some or all of the modules can be selected according to actual needs to achieve the purpose of the solutions of the embodiments. For those persons of ordinary skill in the art can understand and implement the present disclosure without paying creative work.

It should be noted that in the description, relational terms such as "first" and "second" herein are only used to distinguish one entity or operation from another entity or operation, and do not necessarily require or imply that there is any such actual relationship or sequence between these entities or operations. Moreover, the terms "include", "comprise" or any other variants thereof are intended to cover non-exclusive inclusion, so that a process, method, item or device including a series of elements not only includes those elements, but also other elements not explicitly listed, or also include elements inherent to this process, method, item or device. Without further restrictions, the element defined by the sentence "including a . . . " does not exclude the existence of other identical elements in the process, method, item, or device that includes the elements.

The above are only specific embodiments of the present disclosure, so that those skilled in the art can understand or implement the present disclosure. Various modifications to these embodiments will be apparent to those skilled in the art, and the general principles defined herein can be implemented in other embodiments without departing from the spirit or scope of the present disclosure. Therefore, the present disclosure will not be limited to these embodiments shown herein, but will conform to the widest range consistent with the principles and novel features applied herein.

What is claimed is:

1. A method for acquiring inventory data, which is applied to a server, wherein the method comprises steps of:

receiving a request for inventory data sent by a terminal device, wherein electronic tag data of a target item is carried in the request for inventory data;

searching, according to the request for inventory data, among inventory record data pre-stored in a blockchain network for target inventory data corresponding to the electronic tag data, wherein the target inventory data corresponds to the target item; and sending the target inventory data to the terminal device; wherein a connected hospital information system server, an item subcontracting server, and an item management server are deployed in the blockchain network.

2. The method according to claim 1, wherein the target inventory data comprises placement inventory data and shelf inventory data of the target item, and before sending the target inventory data to the terminal device, the method further comprises:

counting a first accumulated value of the placement inventory data and shelf inventory data;

wherein sending the target inventory data to the terminal device comprises:

sending the first accumulated value of the placement inventory data and the shelf inventory data to the terminal device.

3. The method according to claim 2, wherein the target inventory data comprises historical placement inventory data, pending placement inventory data, and placement completion data of the target item, and the placement inventory data is determined by following steps:

counting a second accumulated value of the historical placement inventory data and the pending placement inventory data;

counting a first difference value between the second accumulated value and the placement completion data; and determining the placement inventory data according to the first difference value.

4. The method according to claim 2, wherein the target inventory data comprises historical shelf inventory data, warehousing data, out of warehousing data out of warehousing data, and loss report data of the target item, and the shelf inventory data is determined by following steps:
  counting a third accumulated value of the historical shelf inventory data and the warehousing data;
  counting a second difference value between the third accumulated value and a sum of the out of warehousing data and the loss report data; and
  determining the shelf inventory data according to the second difference value.

5. The method according to claim 4, wherein before sending the target inventory data to the terminal device, the method further comprises:
  acquiring releasing time of the target item; and
  counting the time interval between the releasing time and a preset expiration date of a validity period for the target item;
  wherein sending the target inventory data to the terminal device comprises:
  sending a picking request when the time interval is less than a preset time interval threshold, wherein the picking request is used to request a picking operation for the target item.

6. The method according to claim 1, wherein the method further comprises:
  receiving inventory change data of the target item; and
  updating the inventory record data in the blockchain network according to the inventory change data.

7. A method for acquiring inventory data, which is applied to a terminal device, wherein the method comprises steps of:
  sending a request for inventory data to a server, wherein electronic tag data of a target item is carried in the request for inventory data; and
  receiving target inventory data sent by the server, wherein the target inventory data is searched by the server among inventory record data pre-stored in a blockchain network according to the request for inventory data, wherein the target inventory data corresponds to the target item;
  wherein a connected hospital information system server, an item subcontracting server, and an item management server are deployed in the blockchain network.

8. The method according to claim 7, wherein sending a request for inventory data to a server comprises:
  sending the request for inventory data to the server by calling a chain code and executing a smart contract.

9. A non-transitory computer-readable storage medium, wherein a program for acquiring inventory data is stored on the computer-readable storage medium, and the program, when executed by a processor, causes the processor to perform steps of a method for acquiring inventory data according to claim 1.

10. A non-transitory computer-readable storage medium, wherein a program for acquiring inventory data is stored on the computer-readable storage medium, and the program, when executed by a processor, causes the processor to perform steps of a method for acquiring inventory data according to claim 7.

11. The method according to claim 2, wherein the method further comprises:
  receiving inventory change data of the target item; and
  updating the inventory record data in the blockchain network according to the inventory change data.

12. The method according to claim 3, wherein the method further comprises:
  receiving inventory change data of the target item; and
  updating the inventory record data in the blockchain network according to the inventory change data.

13. The method according to claim 4, wherein the method further comprises:
  receiving inventory change data of the target item; and
  updating the inventory record data in the blockchain network according to the inventory change data.

14. The method according to claim 5, wherein the method further comprises:
  receiving inventory change data of the target item; and
  updating the inventory record data in the blockchain network according to the inventory change data.

* * * * *